United States Patent [19]

Guss et al.

[11] Patent Number: 4,734,524
[45] Date of Patent: Mar. 29, 1988

[54] SYNTHETIC PHEROMONE 8-METHYL-2-DECANOL PROPANOATE

[75] Inventors: Paul L. Guss, Brookings, S. Dak.; James H. Tumlinson, III, Gainesville, Fla.; Philip E. Sonnet, Gainesville, Fla.; Adron T. Proveaux, Gainesville, Fla.

[73] Assignee: The United States of America as represented by the Secretary of Agriculture, Washington, D.C.

[21] Appl. No.: 408,569

[22] Filed: Aug. 16, 1982

[51] Int. Cl.$^4$ .............................................. C07C 69/24
[52] U.S. Cl. ...................................... 560/265; 424/84; 560/261; 568/393; 570/189; 570/217
[58] Field of Search ........................... 560/265; 424/84

[56] References Cited

U.S. PATENT DOCUMENTS 3,717,706 2/1973 McGovern et al. ................... 424/84
4,147,771 4/1979 Struble et al. ......................... 424/84

OTHER PUBLICATIONS

F. P. Cuthbert, Jr., et al., "Studies of Sex Attractant of Banded Cucumber Beetle," J. Econ. Entomol. 57(2): 247–250 (Apr. 1964).

H. J. Ball et al., "A Sex Attractant of the Western Corn Rootworm," J. Econ. Entomol. 66(5): 1051–1053 (Oct. 1973).

P. L. Guss, "The Sex Pheromone of the Western Corn Rootworm (*Diabrotica virgifera*)," Environ. Entomol. 5(2): 219–223 (Apr. 1976).

P. L. Guss et al., "Identification of a Female-Produced Sex Pheromone of the Western Corn Rootworm," J. Chem. Ecol. 8(2): 545–556 (1982).

R. J. Bartelt et al., "Field Studies Involving the Sex-Attractant Pheromones of the Western and Northern Corn Rootworm Beetles," Environ. Entomol. 6(6): 853–861 (Dec. 1977).

*Primary Examiner*—Vivian Garner
*Attorney, Agent, or Firm*—M. Howard Silverstein; David G. McConnell; Curtis P. Ribando

[57] ABSTRACT

A pheromonal compound produced by the western corn rootworm has been identified as 8-methyl-2-decanol propanoate (8-M-2-DP) having the structural formula:

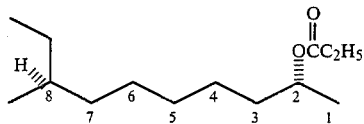

A synthesis has been devised for racemic 8-M-2-DP which demonstrates activity toward the western corn rootworm comparable to its natural counterpart. Other diabroticites including the Mexican corn rootworm and the northern corn rootworm also respond to the synthetic compound. By attracting rootworms to field traps, 8-M-2-DP is a useful tool for the monitoring and control of these major agricultural pests.

3 Claims, No Drawings

SYNTHETIC PHEROMONE 8-METHYL-2-DECANOL PROPANOATE

BACKGROUND OF THE INVENTION

1. Field of the Invention

The genus Diabrotica comprises many of the economically important field pests afflicting U.S. agriculture. In the adult stage the diabroticites, also known as cucumber beetles, inflict damage to a variety of fruits and fruit trees. They also feed on the leaves of cucumber and other vine crops including the squashes (Curcurbita) and melons (Cucumis and Citrullas). The larvae of several species are notorious for their damage to corn crops. The northern corn rootworm (NCR), *D. longicornis barberi* Smith and Lawrence, for instance, is an important corn pest in the upper Mississippi Valley region. The western corn rootworm (WCR), *D. virgifera virgifera* LeConte, and the Mexican corn rootworm (MCR), *D. virgifera zeae* Krysan and Smith, are significant pests in the midwestern and southcentral regions of the United States, respectively.

The continued search for alternatives to the widespread application of insecticides has led to the investigation of sex attractants as potential agents for use in integrated pest management. A number of economically important insects are currently monitored, partially controlled, or completely controlled by use of their own specific sex pheromone. The previous unavailability of Diabrotica pheromones has precluded application of this technology to the treatment of rootworms.

2. Description of the Prior Art

The production of a natural sex attractant by a species of Diabrotica was recognized by Cuthbert, Jr., et al. [J. Econ. Entomol. 57: 247–250 (1964)]. Female abdomen alcohol extracts (10 female equivalents) of the banded cucumber beetle, *D. balteata* LeConte, were reported to lure males of this species from distances as far as 49 ft. (15 m.).

In an unpublished Ph.D. thesis [University of Nebraska, Lincoln (1968)], Cates was able to show that for the WCR a mating or copulation stimulant was produced by 6-day-old virgin females, but he could not conclusively demonstrate the presence of a sex attractant. More recently, Ball et al. [J. Econ. Entomol. 66: 1051–1053 (1973)] reported that hexane extracts from field-collected WCR females were attractive to WCR males under field conditions, but relatively high concentrations of extract (i.e., 500–1,000 female equivalents) were needed for a significant response. These results suggest either the production of a pheromone of low potency, or else a misleading obseervation attributable to the presence of mated females in the field-collected sample. In a subsequent study by Guss [Environ. Entomol. 5: 219–223], it was reported that both WCR males and NCR males responded to an unfractionated hexane extract of filter paper on which WCR virgin females were temporarily held. The agent responsible for the behavior was not determined. Bartelt et al. [Environ. Entomol. 6(6): 853–861 (1977)] confirmed the mutual attractiveness of WCR and NCR males to WCR filter paper extract.

SUMMARY OF THE INVENTION

We have now for the first time obtained in pure or substantially pure form the chemical entity responsible for the pheromonal activity previously observed for WCR extracts. This compound, identified as 8-methyl-2-decanol propanoate (8-M-2-DP) has been isolated from virgin females of the WCR and has also been successfully synthesized. It is an effective attractant for WCR males as well as the males of at least two other major agricultural pests of the Diabrotica genus, the NCR and the MCR. Its usefulness in eliciting a behavioral response when applied to a locus of such males suggests two primary economic applications: (1) the monitoring of existing adult populations in order to predict infestation levels the following year for scheduling of treatment with larval insecticides; and (2) the control of reproduction in adult populations either by direct disruption of mating through confusing or inhibitory properties, or by attracting a demographically significant portion of the male population for subsequent destruction or sterilization.

In accordance with this discovery it is an object of the invention to identify for the first time a sex pheromone from a representative of the family Chrysomelidae, and more particularly from the genus Diabrotica.

It is also an object of the invention to produce racemic 8-M-2-DP as the synthetic counterpart of the natural WCR sex pheromone.

A further object of the invention is to utilize 8-M-2-DP as a monitoring or control agent for economically important species of corn rootworms.

Other objects and advantages of this invention will become readily apparent from the ensuing description.

DETAILED DESCRIPTION OF THE INVENTION

The isolation and identification of the sex pheromone from WCR females has been described in detail in Guss et al. [J. Chem. Ecol. 8(2): 545–556 (1982)], herein incorporated by reference. The male response to 8-M-2-DP of other Diabrotica species including the NCR and MCR suggest that its biosynthesis is not limited to the WCR. Other taxa of lesser agricultural concern also observed to respond to 8-M-2-DP are *D. longicornis longicornis* (Say), a subspecies of the NCR, and *D. porracea* Harold.

The 8-M-2-DP compound of this invention is characterized by the following structural formula:

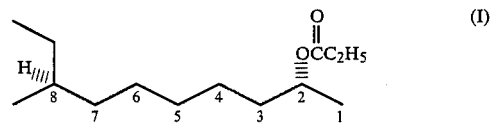

It is apparent therefrom that the compound may exist as any of four stereochemical configurations by virtue of chiral carbons 2 and 8, each accounting for one pair of enantiomers. Present bioassay data indicate that the natural pheromonal compound isolated from the WCR is the 2R,8R stereoisomer. This is also the isomer characterized by the highest activity toward males of the WCR, MCR, and NCR. The 2S,8R isomer is also somewhat active, at least toward the WCR and the MCR. The 2R,8S and 2S,8S configurations are apparently inactive. The scarcity of the natural isolate coupled with the inherent difficulty of directed stereochemical synthesis tends to preclude the commercial utilization of any given isomer in substantially pure form. We have unexpectedly found, however, that the racemic synthetic 8-M-2-DP is equally as active toward the aforementioned rootworms as the natural pheromone when placed in field traps in nanogram quantities. Accordingly, contemplated for use herein is racemic 8-M-2-DP as well as any synthetically produced, configurationally biased mixtures in which at least one of the 2R,8R and the 2S,8R isomers is present in a disproportionately greater amount than the other configurations.

As previously discussed, the synthetic pheromone may be used as either a monitoring agent or a control agent for adult rootworms. In practice, the 8-M-2-DP is used as a trap bait or is otherwise applied to a locus of the adult insects in an amount effective to induce the desired male response. In the case of an attractant response, for example, an effective amount is defined as that quantity of agent which attracts Diabrotica males to the location of a bait at a rate significantly higher than males are attracted to a nonbaited location.

It is envisioned that the 8-M-2-DP would be effective in monitoring or controlling rootworm populations when used in conjunction with any type of trap or pheromone disseminator as known in the art. Typically, the compound would be applied to the device in solution with hexane or other suitable carrier. Volatilization can be retarded by inclusion of an oleaginous extender such as trioctanoin in an amount of approximately 10% of the 8-M-2-DP solution. Slow release may also be effected by encapsulation or absorption into a porous substrate.

Under typical field conditions, at least about $10^{-2}$ μg. of racemic 8-M-2-DP per trap is needed for capturing adult WCR at a statistically significant level. At higher concentrations, the rate at which WCR males are attracted to the vicinity of the traps steadily increases, though the actual number captured may reach a plateau at a level of about 1 mg./trap due to the resultant increase in male-male interactions. With NCR males, a peak response is observed at a concentration of about $10^{-1}$ μg. 8-M-2-DP/trap with an observable response in the range of about $10^{-2}$ to about 10 μg.

The following examples are intended only to further illustrate the invention and are not intended to limit the scope of the invention which is defined by the claims.

EXAMPLE 1

Synthesis of 8-M-2-DP

The synthesis of racemic 8-methyl-2-decanol propanoate, I, as described in the reaction scheme below commenced with the reaction of methyl cyclopropyl ketone and ethyl magnesium bromide. The product was isomerized with HBr (Julia, French Patent No. 1,213,486) producing the homoallylic bromide II (b.p. 76°-82° C. at 30 mm., rep. b.p. 76°-80° C. at 27 mm., yield: 74%). The bromide was converted into a Grignard reagent in ether and added to a stirred suspension of cuprous bromide/dimethyl sulfide [House et al., J. Org. Chem. 40: 1466-1469 (1975)] in an ethereal solution of freshly distilled methyl vinyl ketone. The ketonic product, III, was obtained pure after chromatography on silica gel separated it from dimeric hydrocarbon which formed as a side product during the Grignard preparation. This inverse addition technique gave III in ca. 37% yield from II[IR(CCl4) 1700 cm.$^{-1}$ (C═O)]. Ketone III was reduced with NaBH4 in methanol to give the corresponding alcohol [IR(CCl4) 3560 cm.$^{-1}$ (OH)] which was converted directly to the propionate ester IV using propionyl chloride in pyridine [b.p. 66° C. (bath temp.) at 0.005 mm.; IR(CCl4) 1740 cm.$^{-1}$ (ester C═O); NMR (d6-acetone) 5.0 (m, 1H, vinyl H), 2.28 (g, 2H, J=7, CH3CH2CO2), 1.18 (d, 3H, J=7, CH3CHO), 1.07 p.p.m. (t, 3H, J=7, CH3CH2CO2); yield ca. 80-90% from ketone III]. The saturated ester I was then obtained by hydrogenation over 5% Pd/C in acetic acid [b.p. 60°-65° C. (bath temp.) at 0.005 mm.; IR(CCl4) 1740 cm.$^{-1}$; NMR (d6-acetone) 4.86 (m, 1H, CH3CHO), 2.26 (g, 2H, J=7, CH3CH2CO2), 1.17 (d, 3H, J=7, CH3CHO), 1.06 p.p.m. (t, 3H, J=7, CH3CH2CO2)].

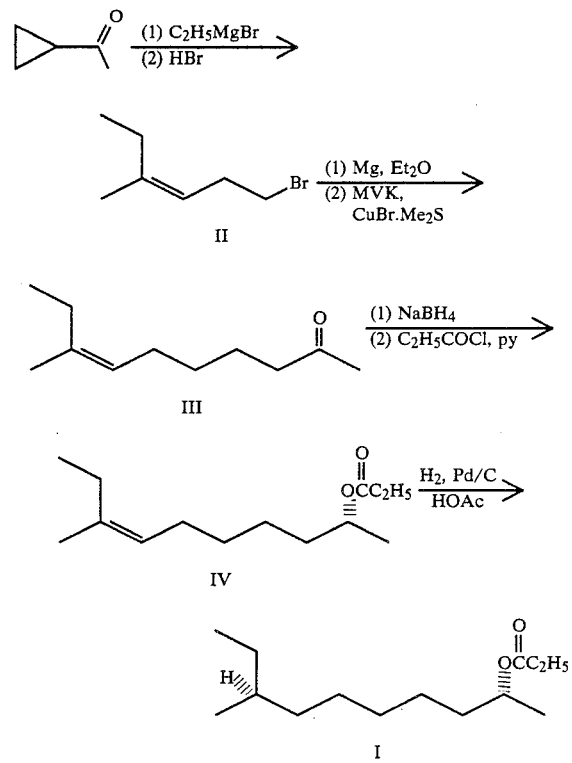

The synthesized racemic 8-methyl-2-decanol propanoate was purified by high-performance liquid chromatography (HPLC) on "Lichrosorb SI60" and subsequently by gas chromatography on "Carbowax 20M." Analysis of the material collected from "Carbowax 20M" by capillary gas chromatography on "OV-101," "SP2340," and cholesteryl cinnamate indicated that it was greater than 99% pure and identical in retention time to the major peak of the active fraction collected from "OV-101" in the isolation of 8-M-2-DP from WCR pheromone extracts. Mass spectral data were obtained with a "Finnegan 3200" mass spectrometer equipped with both electron impact (EI) and chemical ionization (CI) sources. Both the EI and CI spectra of 8-M-2-DP were identical to the respective spectra of the major peak of the natural material.

EXAMPLE 2

The purified racemic 8-M-2-DP obtained by the synthetic procedure of Example 1 was compared in a laboratory bioassay to natural WCR pheromone isolated by the method of Guss et al., spura. Four or five male WCR beetles were placed in a disposable Petri dish (150×15 mm.) and allowed to become acclimated for 15 min. Then either the natural or synthetic material in 1-5 μl. of hexane was applied to a filter paper chip (5 mm.$^2$), and after solvent evaporation (about 10 min.), the treated chip was placed in the Petri dish.

Positive responses consisted or orientation of the beetles toward the chip, distinctive antennal waving, and copulatory behavior toward other males. The behavior elicited from male WCR by the racemic 8-M-2-DP was identical to that observed with the natural pheromone.

EXAMPLE 3

The attractive properties toward the MCR of the purified racemic 8-M-2-DP obtained by the synthetic procedure of Example 1 and unpurified natural WCR pheromone were compared under field conditions. Traps consisting of inverted 360-ml. plastic-coated cups were placed in a corn field on top of wooden stakes spaced 15–20 m. apart such that the top of the trap was about first ear height or about 1 m. from the ground. The interior and exterior of the cups were coated with "Stickem Special" for retaining attracted beetles, and cylindrical cotton wicks (30×10 mm.) were attached to the tops of the traps for dispensing the test materials. Approximately 10 ng. of material in hexane containing 10% trioctanoin was supplied to each of four replicate traps and a pair of control traps was treated with only hexane and the extender. The results from a 24-hour collection period are reported in Table I, below.

EXAMPLE 4

The attractiveness of the purified racemic 8-M-2-DP obtained by the synthetic procedure of Example 1 toward the WCR and NCR were compared under field conditions with that of 90+% pure WCR natural pheromone. Traps similar to those described in Example 3 were placed 15–20 m. apart in a corn field populated by both species. Approximately 350 ng. of material in hexane containing trioctanoin extender was supplied to each of two replicate traps and a pair of control traps was treated with only hexane and the extender. The results of trapping for a continuous 12-day period are reported in Table I, below.

TABLE I

| | | Average number of insects trapped[a] | | |
|---|---|---|---|---|
| Example | Species | 8-M-2-DP | WCR pheromone | Unbaited control |
| 3 | D. virgifera zeae (MCR) | 173[b] | 180[b] | 12 |
| 4 | D. virgifera virgifera (WCR) | 1703[c] | 1868[c] | 19 |
| | D. longicornis barberi (NCR) | 1455[c] | 1339[c] | 145 |

[a]Past experience has shown that traps baited with 8-M-2-DP attract predominantly (>98%) males.
[b]Average of four traps containing about 10 ng. active compound. Data collected for 24-hour period near Beeville, Texas.
[c]Average of two traps containing about 350 ng. active compound. Data collected for continuous 12-day period near Brookings, South Dakota.

EXAMPLE 5

A wide range of levels of racemic 8-M-2-DP prepared as described in Example 1 was tested in the presence of a mixed population of WCR and NCR. Field traps of the type described in Example 3 were employed except that cup-shaped, porous rubber septa were substituted for the cotton wicks for dispensing the 8-M-2-DP solution. After evaporation of the hexane solvent, the absorbed agent was slowly released from the rubber, hereby obviating the need for the trioctanoin extender. The results are reported in Table II, below.

EXAMPLE 6

The effects of 8-M-2-DP on mating of the WCR were tested under field conditions. A 0.1-acre plot isolated from any other corn fields was planted to corn and infested with 2,400 WCR eggs per foot of row. A similar, nonisolated corn field was infested at the same rate with eggs from the same batch. At the onset of adult emergence (determined by pheromone monitoring traps), pheromone sources, 3 m. apart, were placed throughout the entire isolated plot. Each source comprised a 2.7 m. (6 ft.) wooden stake having three rubber septa attached equidistant vertically from ground level to the top. The septa were loaded with 25 mg. of racemic 8-M-2-DP as the hexane solution. Periodically, adults from the two fields were collected and dissected in the laboratory to determine whether or not the females had been inseminated. The results reported in Table III, below, indicate that insemination of available females in the pheromone-treated field occured at a slower rate than that in the control field. As the population increased (to a level of about 10–20 beetles per plant by days 18–20), mating became the same for both fields. It is speculated that this was the result of either increased frequency of chance encounters of males and females or possible to deterioration of the pheromone sources themselves.

TABLE II

| 8-M-2-DP leading (µg./trap) | Beetles trapped[a,b] | | | |
|---|---|---|---|---|
| | WCR | % of total | NCR | % of total |
| $10^{-4}$ | 0 | 0 | | 0 |
| $10^{-3}$ | 0 | 0 | 0 | 0 |
| $10^{-2}$ | 27 | 2 | 1017 | 28 |
| $10^{-1}$ | 144 | 9 | 2187 | 60 |
| 1 | 201 | 12 | 414 | 11 |
| 10 | 243 | 15 | 36 | 1 |
| 50 | 420 | 25 | 0 | 0 |
| 100 | 615 | 37 | 0 | 0 |
| Totals | 1650 | 100 | 3654 | 100 |

[a]Data are corrected for blanks.
[b]Past experience has shown that traps baited with 8-M-2-DP attract predominantly (>98%) males.

TABLE III

| Observation day[a] | Percent of females mated | |
|---|---|---|
| | Pheromone field | Control field |
| 4 | 40 | 93 |
| 11 | 63 | 90 |
| 14 | 69 | 97 |
| 18 | 77 | 82 |
| 22 | 89 | 88 |
| 26 | 88 | 94 |

[a]Recorded from the day on which adult beetles first noted in the pheromone-treated field (day 1).

It is understood that the foregoing detailed description is given merely by way of illustration and that modification and variations may be made therein without departing from the spirit and scope of the invention.

We claim:

1. Substantially pure 8-methyl-2-decanol propanoate as the racemic mixture of its stereoisomers or as an isomeric mixture configurationally biased in favor of at least one of its 2R,8R and 2S,8R stereoisomers.

2. The 8-methyl-2-decanol propanoate of claim 1 as the racemic mixture of its stereoisomers.

3. The 8-methyl-2-decanol propanoate of claim 1 as an isomeric mixture configurationally biased in favor of at least one of its 2R,8R and 2S,8R stereoisomers.

* * * * *